United States Patent [19]

Marion, deceased

[11] Patent Number: 5,007,415

[45] Date of Patent: Apr. 16, 1991

[54] JOINT BRACE

[75] Inventor: DeLos E. Marion, deceased, late of Goodland, Ind., by Martha M. Marion, heir

[73] Assignee: John E. Garber, Indianapolis, Ind. ; a part interest

[21] Appl. No.: 389,696

[22] Filed: Aug. 4, 1989

[51] Int. Cl.$^5$ .............................................. A61F 5/00
[52] U.S. Cl. ................................... 128/80 C; 128/88; 273/189 A; 273/189 R
[58] Field of Search ............... 128/80 R, 80 C, 80 F, 128/80 G, 88; 273/189 R, 189 A

[56] References Cited

U.S. PATENT DOCUMENTS

| | | | |
|---|---|---|---|
| 4,249,524 | 2/1981 | Anderson | 128/80 C |
| 4,632,097 | 12/1986 | Brooks | 128/80 C |
| 4,736,477 | 4/1988 | Moore | 128/88 |
| 4,751,920 | 6/1988 | Mauldin | 128/80 F |
| 4,768,500 | 9/1988 | Mason | 128/88 |
| 4,911,728 | 3/1990 | Rigel | 273/189 A |

Primary Examiner—V. Millin
Assistant Examiner—Philip Kubel
Attorney, Agent, or Firm—Woodard, Emhardt, Naughton, Moriarty & McNett

[57] ABSTRACT

A brace for a human joint. The brace includes a top clamp and a bottom clamp removably mountable to the limbs on the opposite sides of the joint and secured thereto by a pair of belts. A plurality of adjacent strips have top ends fixedly mounted to the top clamp and bottom ends slidably mounted to the bottom clamp. The bottom clamp includes a pin fixedly mounted thereto which extends through a slot in the strips facilitating slidable motion for the strips relative to each other and with respect to the bottom clamp. An elastic housing encloses the top clamp, bottom clamp and a portion of the strips urging the bottom clamp towards the top clamps, but yieldable to allow further separation.

16 Claims, 4 Drawing Sheets

JOINT BRACE

BACKGROUND OF THE INVENTION

1. Field of the Invention:

This invention is in the field of braces for human joints.

2. Description of the Prior Art:

A variety of mechanical braces have been devised for supporting a joint allowing pivotal motion thereof. Braces have been particularly utilized in supporting the knee joint to facilitate knee pivotal motion. Typically, the knee brace is mounted immediately above and beneath the knee and extends along the opposite sides thereof. Such a knee brace has a fixed pivot axis which must be initially aligned with the knee pivot axis. After repeated pivotal motion of the knee, the brace may shift longitudinally on the leg resulting in misalignment of the brace pivot axis relative to the knee pivot axis. Undue pressure is then applied to the knee joint due to the misalignment of the two pivot axes. To further compound such a problem, the knee joint pivot axis floats or moves during any knee motion while the pivot axis of the prior art knee brace is fixed due to the construction extending on the opposite sides of the knee. I have disclosed herein a joint brace particularly adapted for use with the knee which has a floating or non-fixed brace pivot axis aligned with the knee pivot axis even though the knee is constantly moving and the brace has shifted from its initial mounting location.

The knee brace disclosed herein is designed to prevent injuries particularly occurring in sporting activities as distinguished from many prior braces designed to support the joint after joint injury. These prior art braces are relatively heavy structures extending on the opposite sides of the joint and will therefore transmit lateral impact force directly to the joint. The brace disclosed herein does not extend on the opposite sides of the joint, but is instead located forward of the joint. Further, my brace includes a plurality of slidably mounted strips extending above and below the joint providing resistance to twisting of the joint.

SUMMARY OF THE INVENTION

One embodiment of the present invention is a brace for a human joint comprising a bending device positionable adjacent a human joint and being operable to limit movement of the joint in certain directions but allowing pivoting action of the joint about a joint pivot axis, the bending device having a first end and an opposite second end and including a plurality of bendable strips extending therebetween being slidably mounted together in side by side relationship and bendable about a non-fixed strip axis, a first mount on the first end of the bending device operable to mount the brace on one side of the human joint and limit relative motion between the first end and the one side, and, a second mount on the second end of the bending device operable to mount the brace on the other side of the human joint and limit relative motion between the second end and the other side.

Another embodiment of the present invention is a method of supporting with a brace a human joint located between a first limb element and a second limb element comprising the steps of: fixedly mounting the top end of the brace to the first limb element to limit relative motion therebetween, fixedly mounting the bottom end of the brace to the second limb element to limit relative motion therebetween, positioning a supporting strip with a non-fixed and floating axis which may move as the joint pivots allowing pivoting action of the joint but limiting movement of the joint in certain directions and located adjacent to the joint being fixedly attached to the top end and slidably attached to the bottom end, and, locating the strip on the side of joint opposite of pivotal motion of the first limb element and the second limb element.

It is an object of the present invention to provide a new and improved brace for a human joint.

A further object of the present invention is to provide a new and improved method of supporting with a brace a human joint.

In addition, it is an object of the present invention to provide a joint brace having a floating bend axis.

Further, it is an object of the present invention to provide a joint brace having a bend axis automatically aligned with the joint pivot axis.

Related objects and advantages of the present invention will be apparent from the following drawings.

DESCRIPTION OF THE PREFERRED EMBODIMENT

Figure 1:
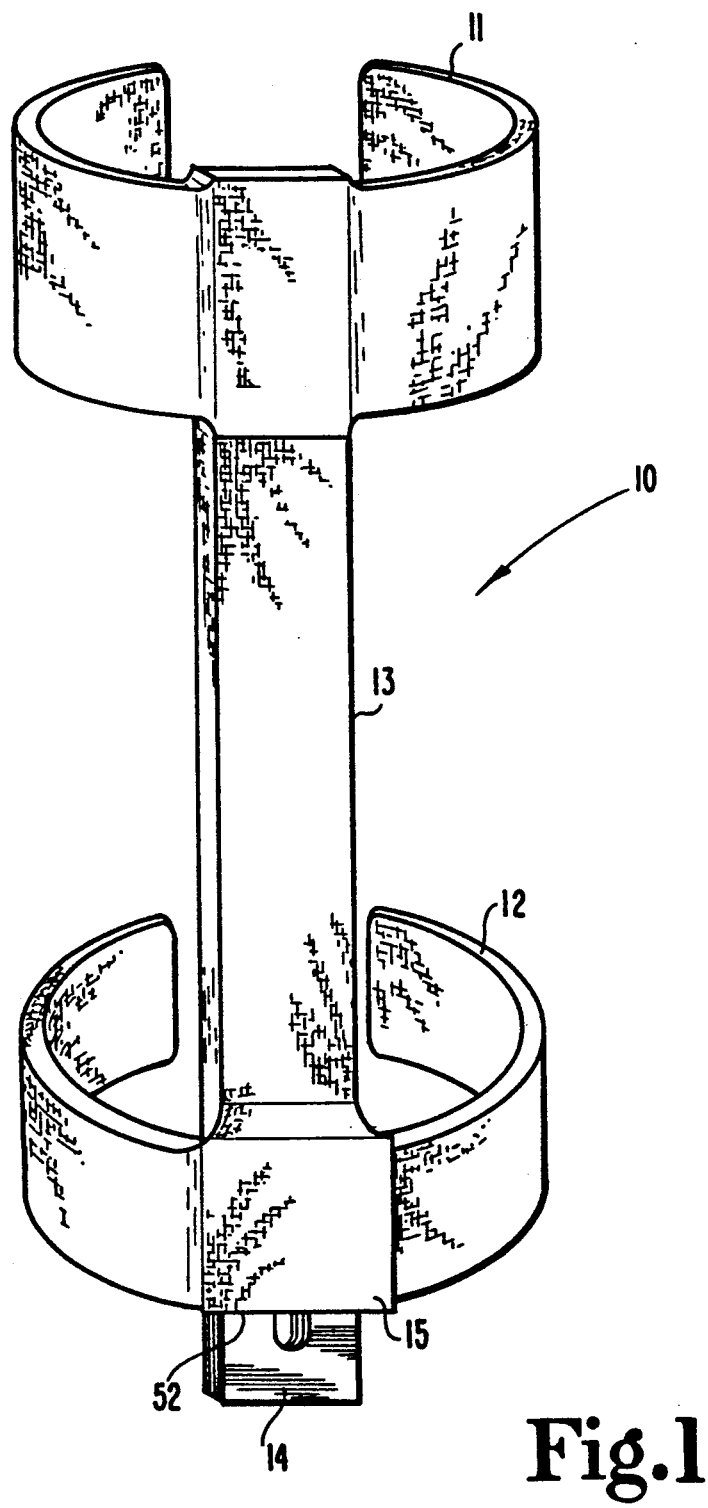
FIG. 1 is a perspective view of the brace incorporating my new invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to FIG. 1, there is shown a brace 10 mountable to a human joint by means of a top C-shaped clamp 11 and a bottom C-shaped clamp 12. The top clamp 11 and the bottom clamp 12 are mounted, respectively, fixedly and slidably to an elongated main body 13 formed by a stack 14 of strips. An elastic spring covering 15 encases stack 14 along with the clamps 11 and 12.

Figure 2:
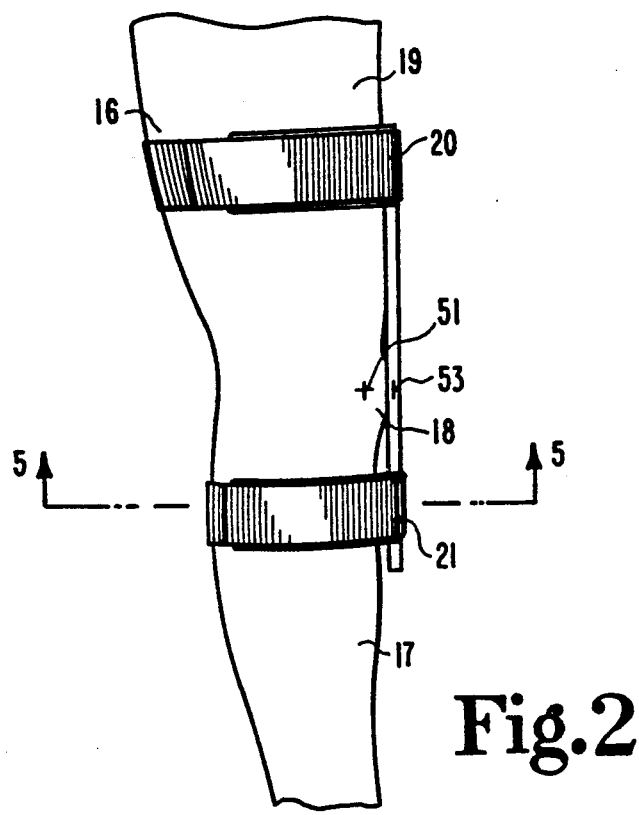
FIG. 2 is a side view of the brace mounted to a knee with the leg shown in the extended position.
Figure 3:
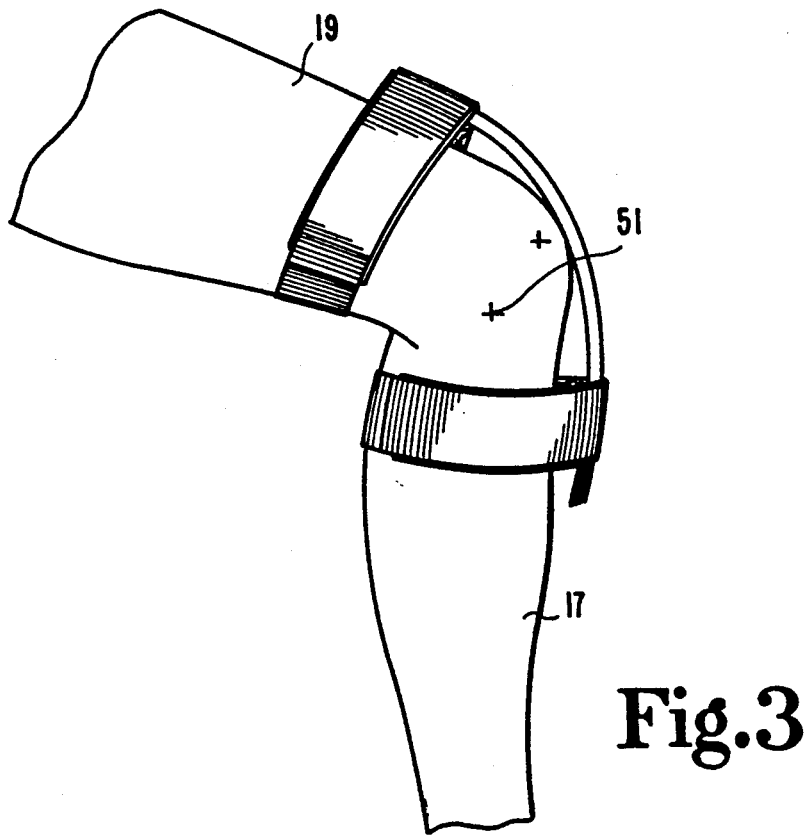
FIG. 3 is the same view as FIG. 2, only showing the leg in a bent position.
Figure 5:
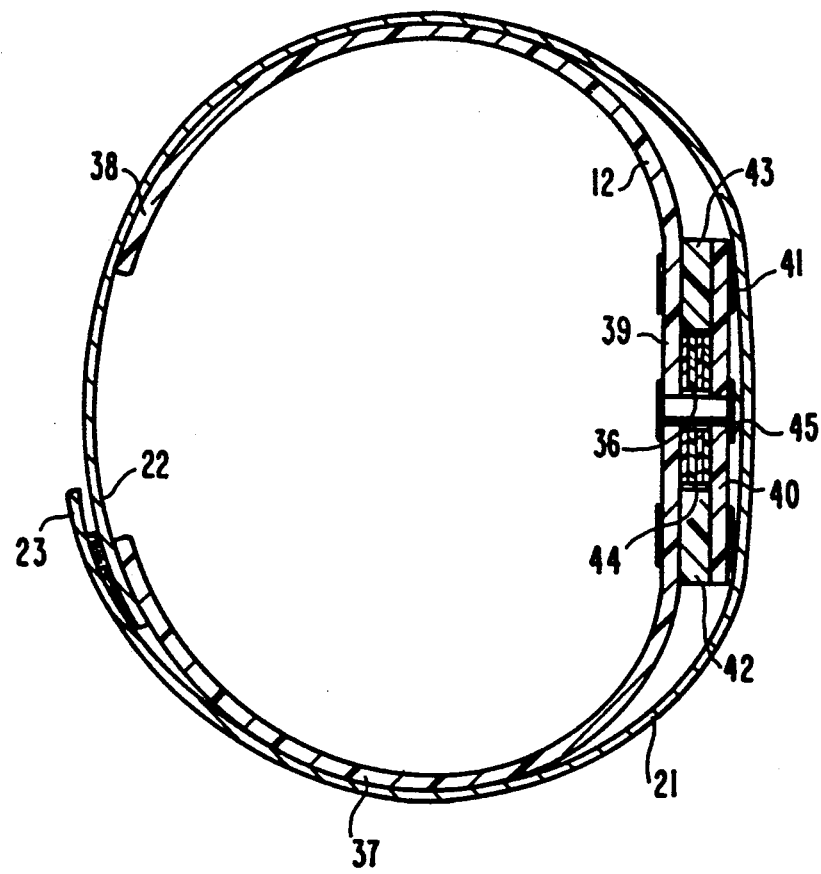
FIG. 5 is an enlarged cross-sectional view taken along the line 5—5 of FIG. 4 and viewed in the direction of the arrows.

FIGS. 2 and 3 show, respectively, the brace of FIG. 1 mounted to a leg in an extended and bent condition. The top clamp 11 and bottom clamp 12 each have a pair of opposed spring legs which will separate allowing the leg to be positioned within the clamp with the legs of each clamp then springing back together around the leg to fixedly mount the brace to the leg. The brace is oriented so the stack 14 of strips is positioned forward and immediately adjacent the knee 18. To ensure the brace does not move longitudinally on leg 19, a conventional fabric belt 20 is extended around the top portion 16 of the leg immediately adjacent and around top clamp 11. The opposite ends of fabric belt 20 include mating fasteners, such as synthetic materials which adhere when pressed together identified by the trademark Velcro ®, thereby allowing the opposite ends of belt 20 to be securely fastened together fixedly mounting clamp 11 to the leg. Similarly, a fabric belt 21 identical to belt 20 is mounted to the bottom portion 17 of the leg to extend around and adjacent bottom clamp 12 with the opposite ends of belt 21 being fastened together thereby securely mounting the brace and the bottom clamp to the leg. A cross-sectional view of the brace is shown in FIG. 5 depicting belt 21 extending around the brace and immediately adjacent the bottom clamp 12 with the opposite ends 22 and 23 of the belt being removably secured together by conventional fastening devices securely mounting the brace and bottom clamp to the leg. The top belt 20 is removably mounted to the top clamp 11 and brace in the manner similar to that depicted in FIG. 5.

Figure 4:
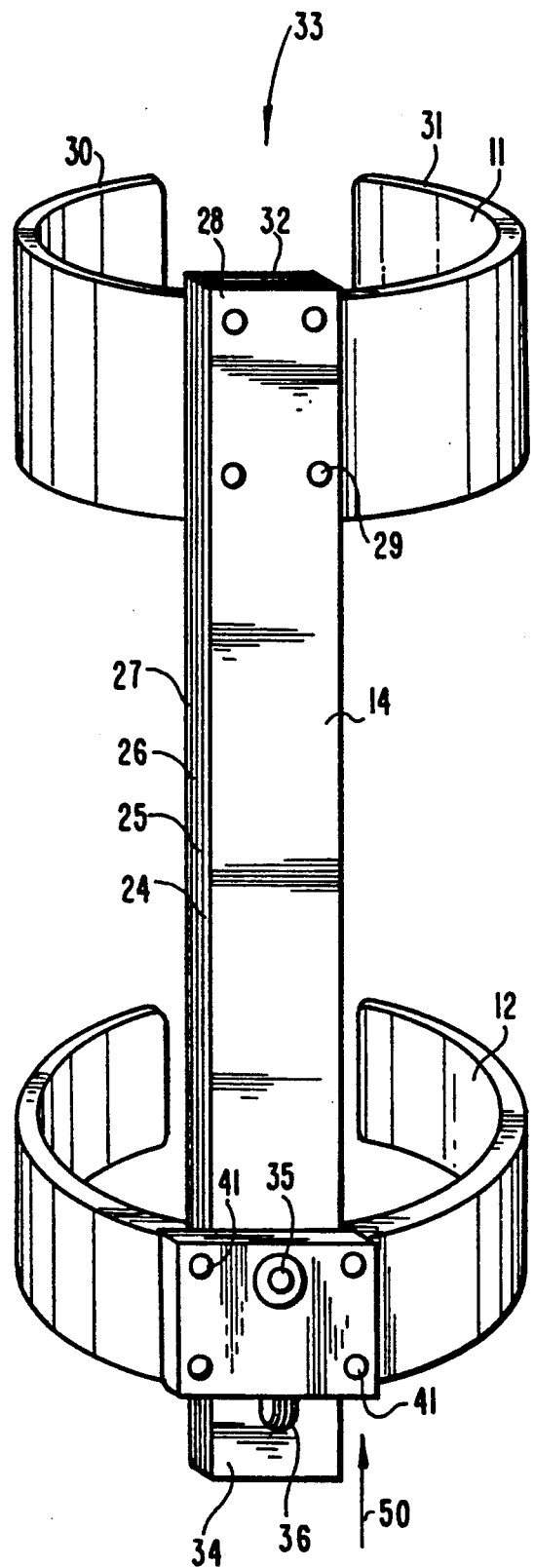
FIG. 4 is a perspective view of the brace of FIG. 1 with the outer elastic covering removed therefrom.

The elastic covering or spring means 15 has been removed from clamps 11 and 12, and stack 14 in FIG. 4 to more clearly illustrate the interior structure. Stack 14 includes in the embodiment shown in FIG. 4, four separate strips 24, 25, 26 and 27 each having a top end 28 fixedly secured by conventional fasteners 29 to the top clamp 11. The top clamp includes a pair of opposed arms 30 and 31 integrally joined to a flat portion 32 in turn secured by fasteners 29 to the strips. The distal ends of arms 30 and 31 are spaced apart forming opening 33 through which the top portion 16 of the leg may be extended with the legs being pulled apart as the leg passes through opening 33 and then released to surround the leg.

The bottom ends 34 of strips 24 through 27 are slidably mounted to bottom clamp 12 by means of a pin 35 extending through a slot 36 formed in the four strips. Referring to FIG. 5, bottom clamp 12 includes a pair of opposed arms 37 and 38 integrally joined to a flat portion 39 with the distal ends of arms 37 and 38 being spaced apart to allow the bottom portion 17 of the leg to pass therethrough so that the arms 37 and 38 will surround the leg securing the brace thereto. Flat portion 39 is affixed to an outer wall 40 by conventional fastening devices 41. A pair of spacers 42 and 43 are positioned between flat portion 39 and outer wall 40 thereby creating a passage 44 through which bottom end 34 of stack 14 extends and is freely slidable. Fasteners 41 extend through outer wall 40, spacers 42 and 43, and flat portion 39 of the bottom clamp. Further, a pin 35 is fixedly secured to outer wall 40 and flat portion 39 of the clamp and extends centrally through passage 44. Pin 35 also extends freely through slot 36 which is formed in strips 24, 25, 26 and 27. Passage 44 and pin 35 thereby guide strips 24 through 27 as the strips slide relative to the pin and clamp 12. Slot 36 has a lateral width greater than pin 35 to prevent interference between the strips 24 through 27 and pin 35. Slot 36 has a closed top end and closed bottom end to prevent the strips from escaping from pin 35 and passage 44. The head 45 of pin 35 has an outside diameter greater than the width of slot 36.

The brace is mounted adjacent and in front of the joint on the side thereof opposite from the pivotal motion of the joint. Thus, in the case of mounting the brace to a leg, the stack 14 of strips is positioned in front of knee 18 (FIG. 2) on the side of the leg opposite the direction of pivotal motion of the leg as depicted in FIG. 3. Belts 20 and 21 secure, respectively, the top and bottom clamps to the upper portion 16 and lower portion 17 of the leg preventing the clamps from shifting longitudinally on the leg as the knee is flexed about the knee joint 18. As the leg pivots about knee 18 from the erect position of FIG. 2 to the bent position of FIG. 3, the stack 14 of strips will move upwardly relative to clamp 12 in the direction of arrow 50 (FIG. 4) within passage 44. Due to the greater distance of the outer strip 24 from the knee, the outer strip 24 will slide a greater distance in the direction of arrow 50 than strip 25 which in turn will slide a greater distance in the direction of arrow 50 than strip 26. Since the inner strip 27 is immediately adjacent the leg, pressure is applied by the knee directly to the inner strip and in turn to the remaining strips causing the stack of strips to bend or pivot as the knee is flexed from the position of FIG. 2 to the position of FIG. 3. As the knee pivots from the position of FIG. 2 to the position of FIG. 3, the knee pivot axis 51 moves rearwardly and downwardly. Such a shift is caused by the mating of the downwardly facing concave surface of the femur and the rounded top end of the tibia. The concave surface is not perfectly round and thus the tibia or bottom portion of the knee joint rolls and slides backward as the knee flexes moving the knee pivot axis downwardly and rearwardly. Thus, even though the pivot axis 51 (FIG. 2) of the knee shifts during pivotal motion of the knee, the brace will automatically compensate due to the knee pressure onto the strips and the sliding motion of the strips relative to the bottom clamp and will be pivotally aligned therewith. Further, there is no need to initially align the pivot axis of the brace with the pivot axis of the knee. Further, in the unlikely event that the brace slips longitudinally on the leg, the stack of strips will automatically compensate since the inner strip 27 is in direct contact with the knee and will be forced to pivot or bend accordingly.

Elastic covering 15 extends completely around and encloses the arms of clamps 11 and 12, and likewise extends completely around stack 34 on the top end thereof and all sides, with the exception that the stack of strips is allowed to freely slide and project through the bottom end 52 of the elastic covering.

The stack of strips provides a bending means which is positionable adjacent a human joint including, for example, the human knee and is operable to limit movement of the joint in certain directions including a twisting direction, while at the same time allowing the joint to pivot about its normal axis. The stack includes a plurality of bendable strips which are slidably mounted together in a side-by-side relationship about a strip axis automatically aligned with the joint pivot axis even though the joint pivot axis moves during joint movement. That is, the stack of strips will bend about axis 53 (FIG. 2) which is initially aligned with joint pivot axis 51. In the event axis 51 moves during joint movement then axis 53 will compensate and automatically be aligned therewith since the joint is forced against the inner strip of the stack and forces the stack of strips to bend and slide accordingly. The upper and lower clamps along with belts 20 and 21 provide a means for mounting the opposite ends of the stack of strips to limit relative motion between the clamps and the limbs extending on the opposite sides of the joint.

The elastic covering 14 provides a spring means extending between the two clamps and is operable to urge the bottom clamp toward the top clamp, but yieldable to allow the bottom clamp to move relative to the top clamp changing the distance therebetween. The elastic covering may be produced from an elastic fabric material whereas strips 24 through 27 may be produced from plastic or metal having sufficient flexibility to allow for the bending motion previously described. Likewise, the number of strips can be varied from that shown and described. Covering 15 surrounds clamp 12 and wall 40, but allows the strips to extend freely therefrom.

The method of supporting with a brace a human joint located between a first limb and a second limb includes the step of fixedly mounting the top end of the brace to the upper limb to limit relative motion therebetween and then fixedly mounted the bottom end of the brace to the second limb to limit relative motion therebetween. A plurality of strips fixedly attached at the top end of the brace and slidably mounted to the bottom end of the brace are then positioned adjacent the joint on a side opposite of the pivotal motion of the joint. The strips have a non-fixed and floating pivot or bend axis depending upon the joint pressure on the inner strip. The strips slide relative to each other as the joint pivots with an elastic housing biasing the bottom end of the brace towards the top end of the brace, but yieldable to allow the opposite ends of the brace attached to the limbs to lengthen.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A brace for a human joint comprising:
bending means positionable adjacent a human joint and being operable to limit movement of said joint in certain directions but allowing pivoting action of said joint about a joint movable pivot axis, said bending means having a first end and an opposite second end and including a plurality of bendable strips extending therebetween being slidably mounted together in side by side relationship and bendable about a non-fixed strip axis;
first mounting means on said first end of said bending means operable to mount the brace on one side of said human joint and limit relative motion between said first end and said one side; and,
second mounting means on said second end of said bending means operable to mount the brace on the other side of said human joint and limit relative motion between said second end and said other side.

2. The brace of claim 1 wherein:
said strips are movably secured to said first mounting means at said first end allowing relative motion between said strips and said first mounting means while said first mounting means and said second mounting means remain stationary relative respectively to said one side and said other side of said joint.

3. The brace of claim 1 wherein:
said strips are fixedly secured to said second mounting means at said second end limiting relative motion at said second end between said strips and said second mounting means.

4. The brace of claim 3 wherein:
said strips are slidably mounted to said first mounting means but non-slidable relative to said second mounting means.

5. The brace of claim 1 and further comprising:
spring means extending between said said first mounting means and said second mounting means operable to urge said first mounting means toward said second mounting means but yieldable to allow said first mounting means to move relative to said second mounting means changing the distance therebetween.

6. The brace of claim 1 and further comprising:
fastening means slidably mounting said first mounting means to said strips at said first end.

7. The brace of claim 6 wherein:
said first mounting means includes a guide passage through which said strips extend guiding said strips relative thereto, said first mounting means further includes a pin and said strips have aligned slots through which said pin extends to allow slidably motion between said strips and said first mounting means.

8. A brace for a human joint located between a first limb element and a second limb element comprising:
a first brace mount removably mountable to the first limb element;
a second brace mount removably mountable to the second limb element; and,
an elongated bending means connecting said first brace mount and said second brace mount together, said bending means positionable adjacent the joint on a side opposite of pivotal motion of said first limb element and said second limb element and having one end secured to said first brace mount and a second end slidably secured to said second brace mount, said bending means being operable to bend about a non-fixed and floating axis which may move as the joint pivots allowing pivoting action of said joint but limiting movement of said joint in certain directions; and
wherein: said bending means includes a stack of strips with first ends fixedly fastened in non-slidable relationship to said first brace mount and opposite second ends slidably mounted to said second brace mount.

9. The brace of claim 8 wherein:
said second brace mount includes a passage slidably receiving said stack of strips with said second brace mount and said stack cooperatively including a slot and pin combination wherein individual strips of said stack are allowed to slide different amounts relative to said second brace mount as said joint pivots.

10. The brace of claim 9 and further comprising:
spring means attached to said first brace mount and said second brace mount operable to urge said second brace mount toward said first brace mount but yieldable to allow movement of said second brace mount in a direction away from said first brace mount.

11. A method of supporting with a brace a human joint located between a first limb element and a second limb element comprising the steps of:
fixedly mounting the first end of the brace to said first limb element to limit relative motion therebetween;
fixedly mounting the second end of the brace to said second limb element to limit relative motion therebetween;

positioning a supporting strip with a non-fixed and floating bend axis which may move as the joint pivots allowing pivoting action of said joint but limiting movement of said joint in certain directions and located adjacent to said joint being fixedly attached to said first end and slidably attached to said second end; and, locating said strip on the side of joint opposite of pivotal motion of said first limb element and said second limb element.

12. The method of claim 11 and comprising the further step of:

spring biasing said second end of said brace toward said first end of said brace being yieldable to allow said second end to move relative to said first end.

13. The method of claim 12 wherein:

said positioning step includes positioning a plurality of supporting strips in a stack adjacent to said joint being fixedly attached to said first end and slidably attached to said second end with said strips sliding relative to each other as said joint pivots.

14. A brace for a human joint comprising:

bending means positionable adjacent a human joint and being operable to limit movement of said joint in certain directions but allowing pivoting action of said joint about a joint movable pivot axis, said bending means having a first end and an opposite second end and including a bendable strip extending therebetween being slidably mounted and bendable about a non-fixed strip axis;

first mounting means on said first end of said strip operable to mount the brace on one side of said human joint and limit relative motion between said first end and said one side; and, second mounting means on said second end of said strip operable to mount the brace on the other side of said human joint and limit relative motion between said second end and said other side.

15. The brace of claim 14 wherein:

said strip is movably secured to said first mounting means at said first end allowing relative motion between said strip and said first mounting means while said first mounting means and said second mounting means remain stationary relative respectively to said one side and said other side of said joint.

16. The brace of claim 14 wherein:

said strip is fixedly secured to said second mounting means at said second end limiting relative motion at said second end between said strips and said second mounting means.

* * * * *